United States Patent [19]

Hess et al.

[11] Patent Number: 4,745,214

[45] Date of Patent: May 17, 1988

[54] PROCESS FOR THE PREPARATION OF AN AQUEOUS SOLUTION OF UNSATURATED QUATERNARY AMMONIUM SALTS

[75] Inventors: Raymond Hess, Forbach; Christian Lacroix, Forkling, both of France

[73] Assignee: Norsolor, Paris, France

[21] Appl. No.: 876,602

[22] Filed: Jun. 20, 1986

[51] Int. Cl.[4] .............................................. C07C 69/52
[52] U.S. Cl. .................................... 560/222; 564/204; 564/207
[58] Field of Search ................ 560/222; 564/204, 207

[56] References Cited

U.S. PATENT DOCUMENTS 4,362,890  12/1982  Oshima et al. ...................... 560/222

FOREIGN PATENT DOCUMENTS 573175  11/1945  United Kingdom ................ 560/215

Primary Examiner—Paul J. Killos
Attorney, Agent, or Firm—Millen & White

[57] ABSTRACT

For the preparation of an aqueous solution of unsaturated quaternary ammonium salts of the formula (I):

$$H_2C=C-(R_3)C(O)-A-R_4-N^{\oplus}(R_1)(R_2)(R).X^{\ominus},$$

e.g., methacryloyloxyethyltrimethylammonium chloride
the steps of:
(a) reacting a (meth)acrylic monomer, e.g., dimethylaminoethyl methacrylate in a closed reactor, in the presence of a polymerization inhibitor, e.g., 3,5-ditert-butyl-4-hydroxytoluene, with 5 to 20% of the weight quantity of quaternizing agent, e.g., methylchloride, required for the reaction, wherein the latter agent is introduced into the reactor continuously,
(b) adding water and the remainder of the quaternizing agent continuously until the required concentration of quaternary ammonium salt in water is obtained,
(c) maintaining the temperature at a value of between 30° and 60° C. during the stages (a) and (b), and
(d) maintaining a stream of gas containing oxygen in the reaction mixture during the stages (a) and (b) and especially as the end of the reaction approaches, such that the volume ratio of gas at the reactor outlet to the oxygen introduced at the inlet of this same reactor is less than 100/1.

40 Claims, No Drawings

PROCESS FOR THE PREPARATION OF AN AQUEOUS SOLUTION OF UNSATURATED QUATERNARY AMMONIUM SALTS

The present invention relates to a process for the preparation of an aqueous solution of unsaturated quaternary ammonium salts (called quaternary salts hereinafter) corresponding to the following general formula (I):

$$H_2C=C(R_3)-C(O)-A-R_4-N^{\oplus}(R_1)(R_2)(R).X^{\ominus}$$

in which:
A is an oxygen atom or an NH group,
$R_3$ is a hydrogen atom or a methyl radical,
$R_4$ is a linear or branched alkyl radical containing from 2 to 4 carbon atoms,
$R_1$ and $R_2$, which are different or identical, are an alkyl radical or an aryl radical,
R is an alkyl or aryl radical, and
X is chosen from Cl, Br, I, $-CH_3-CO_3$ or $-CH_3-SO_4$,
the quaternary salts (I) being obtained by reacting a (meth)acrylic monomer (II) of general formula:

$$H_2C=C(R_3)-C(O)-A-R_4-N(R_1)(R_2)$$

with a quaternizing agent (III) of formula RX.

Aqueous solutions of quaternary salts (I) are used for preparing polymers intended for use as flocculants in water treatment.

The principal problems which arise during the synthesis of quaternary salts (I) are, on the one hand, the water-sensitivity of the monomers (II) and, on the other hand, the risks of polymerization of the reaction mixture in the reactor and those of the quaternary salts (I) during storage.

In order to solve these problems, many syntheses of quaternary salts (I), which follow the principle described above, have been developed.

A first category of syntheses proposes the use of organic solvents such as acetone (Japanese Patent Application No. 60/054,343) or ketonic solvents (German Patent Application No. 3,244,274), which make it possible to restrict or even to eliminate contacts between water and monomers (II) and hence to reduce the phenomena of hydrolysis of the latter. When the operation has ended, the aqueous phase comprising the quaternary salt (I) is recovered, for example by phase separation. This aqueous phase must then be purified in order to remove the traces of solvents which carry a risk, on the one hand, of interfering with the polymerization of the quaternary salt (I) and, on the other hand, of compromising the performance of these polymers when they are used, especially as a flocculant.

In a second category of syntheses, the quaternization of the monomers (II) is carried out in a solely aqueous solution. Thus, a process has been proposed according to which a monomer (II) is reacted at an initial concentration in water of at least 80% by weight and capable of reaching 100% by weight (see G.B. Pat. No. 1,538,265). It is found, in fact, that at such concentrations the phenomena of hydrolysis of the monomers (II) are considerably reduced. However, the process described in G.B. Pat. No. 1,538,265 leads, during the synthesis, to the formation of supersaturated solutions of quaternary salts (I). As a result, precipitation of salt crystals and deposits of crystals occur on the reactor walls, especially on the cooling surface provided for removing the heat of reaction. These deposits give rise to problems of two principal types. On the one hand, as indicated earlier, they compromise the cooling of the reaction mixture. On the other hand, by going beyond the saturation point, one obtains a reaction medium characterized by a high viscosity and a considerable reduction in the reaction kinetics. On a laboratory scale these problems pass relatively unnoticed; on an industrial scale, on the other hand, they are reflected in poor control of the reaction temperature with runaways of the reactor temperature, which are prejudicial to the stability of the quaternary salt (I) to polymerization when it is stored.

It is known that the presence of a sufficient quantity of oxygen enables polymerization processes to be inhibited. Nevertheless, the application of this property on an industrial scale is far from satisfactory at present. When the known quaternization processes are used, one is currently faced with the possibility of a polymerization of the quaternary salt (I) during its manufacture or during its storage. For this reason, it is common practice to prepare aqueous solutions of quaternary salts (I) in reactors of moderate size, generally less than 10 $m^3$, in order to limit the losses, should the reaction mixture polymerize.

The subject of the present invention is a process for the preparation of an aqueous solution of unsaturated quaternary salts corresponding to the general formula (I) indicated above, and especially concentrated aqueous solutions of these salts (I), which process does not present the problems of viscosity or of hydrolysis of the monomer (II) described earlier, and which makes it possible to eliminate the danger of polymerization of the reaction mixture during the synthesis and that of the aqueous solutions of the quaternary salt (I) which are obtained. The soutions obtained are characterized by a stability at ambient temperature which is longer than one year.

More precisely, the subject of the invention is a process for the preparation of an aqueous solution of unsaturated quaternary ammonium salts corresponding to the general formula (I) from at least one (meth)acrylic monomer (II) and at least quaternizing agent (III), in the presence of at least one polymerization inhibitor, in which process:

(a) the (meth)acrylic monomer (II) is reacted in a closed reactor with 5 to 20% of the weight quantity of quaternizing agent (III) required for the reaction, this agent being introduced into the reactor continuously, (b) next, water and the remainder of the quaternizing agent (III) are added continuously until the required concentration of quaternary ammonium salt (I) in water is obtained, (c) during the stages (a) and (b) the temperature is maintained at a value of between 30° and 60° C., and (d) during the stages (a) and (b) and especially as the end of the reaction approaches, a stream of gas containing oxygen is maintained in the reaction medium, such that the volume ratio of gas at the reactor outlet to the oxygen introduced at the inlet of this same reactor is less than 100/1.

Preferably, a ratio by volume of gas leaving the reactor to the oxygen introduced at the inlet of this reactor of less than 50/1 is imposed during the reaction.

In accordance with a different embodiment of the process according to the invention, (a') the (meth)acrylic monomer (II) and 5 to 20% by weight of an aqueous solution of quaternary salt (I) comprising from 50 to 80% by weight of quaternary salt are introduced into a closed reactor, the operating conditions b, c and d remaining, in their case, identical to those recommended in the invention above.

In order to avoid supersaturation of the reaction mixture with quaternary salt (I), a molar ratio of addition of water to the quaternizing agent (III) of between 2.2 and 3.7 is imposed during stage (b). Below 2.2, a viscous reaction mixture is obtained with its temperature being difficult, or even impossible, to control. On the other hand, at a value above 3.7, there is considerable danger of hydrolysis of the (meth)acrylic monomer (II).

A temperature of between 45° C. and 55° C. is preferably maintained during the stages (a), (a') and (b).

Also preferably, approximately 10% by weight of a quaternizing agent (III) or of an aqueous solution of quaternary salt (I) comprising 50 to 80% by weight of quaternary salt, respectively, are introduced during the stage (a) or (a') indicated earlier. It is in this preferred embodiment, in fact, that the best reaction kinetics and the most satisfactory viscosity are obtained.

The process according to the invention is preferably carried out at a pressure between atmospheric pressure and 1.6 bars absolute pressure. In point of fact, at higher pressure values the solution of quaternary salt (I) is not stable on storage and sometimes even polymerizes at the end of the operation.

When the quaternizing agent (III) is a volatile compound which is gaseous at the temperature of the reaction, the introduction of the quaternizing agent during the reaction is performed so as to limit its losses in purge. The losses are thus kept below 10% (molar) of the stoichiometry.

The gas leaving the reactor is then led to a processing device intended to free it of traces of the quaternizing agent (III) which it contains, especially in the case where the latter has a high vapor pressure or is volatile at the temperature of reaction. Preferably, the gas is conveyed to a second reactor containing (meth)acrylic monomer (II) in which the quaternizing agent (III) is trapped.

At the end of reaction the traces of quaternizing agent (III) dissolved in the reaction mixture are removed by purging the latter with a strong current of oxygen-containing gas, for example air.

The process according to the invention is used for the quaternization of (meth)acrylic monomers (II) (refer to the formula indicated earlier). However, this process is more particularly intended for (meth)acrylic monomers (II) which are easily capable of being hydrolyzed and which are liable to polymerize readily. Among the latter there may be mentioned dimethylaminoethyl acrylate, dimethylaminopropyl acrylate, dimethylaminoethyl methacrylate, dimethylaminopropyl methacrylate, dimethylaminopropylacrylamide and dimethylaminopropylmethacrylamide.

The quaternizing agents (III) which are suitable for the present invention are especially halogenated hydrocarbons such as methyl chloride, methyl bromide, methyl iodide, ethyl chloride, ethyl bromide, ethyl iodide or benzyl chloride; and dimethyl sulfate or dimethyl carbonate.

Among the stabilizers (or polymerization inhibitors) which may be used in the process according to the invention, there may be mentioned 3,5-ditert-butyl-4-hydroxytoluene, hydroquinone methyl ether, phenothiazine, hydroquinone, catechol and tert-butylcatechol or a mixture of these stabilizers. Preferably, from 100 to 1,500 ppm of stabilizer are used relative to the (meth)acrylic monomer (II). Research carried out by the Applicant Company on this subject has shown that good results are obtained by using from 1,000 to 1,500 ppm of 3,5-ditert-butyl-4-hydroxytoluene or 500 to 1,000 ppm of hydroquinone methyl ether, or 70 ppm of phenothiazine, these quantities being expressed relative to the quantity of (meth)acrylic monomers (II).

The process according to the invention makes it possible to prepare aqueous solutions of quaternary salts (I), particularly at concentrations of 50 to 85% by weight of salts (I) in water. The quaternary salt (I) solutions thus obtained contain small quantities of hydrolysis products of the monomers (II) and thus require no additional purification. These solutions have a stability in storage at ambient temperature of more than one year.

In addition, as a result of the good reproducibility of the process according to the invention, especially of the stability of the reaction mixture, the quaternization operations are carried out in reactors of large capacity, of the order of 20 to 50 m$^3$.

The examples which will follow and which are given by way of indication, will enable the invention to be better understood. In these examples, the percentages shown are % by weight.

EXAMPLE 1 (comparative)

Preparation of a 75% strength aqueous solution of methacryloyloxyethyltrimethylammonium chloride 360 kg of dimethylaminoethyl methacrylate containing 1,000 ppm of hydroquinone methyl ether are charged with stirring into a jacketed reactor.

After the reactor has been pressurized with air to 1.6 bars absolute, methyl chloride and water are introduced continuously in a water/CH$_3$Cl weight ratio of 1.3 (ie a molar ratio of 3.6). The reaction is carried out at 40° C. and at a pressure which gradually rises to 5 bars absolute at the end of the reaction.

In this example, the quaternization is carried out without the purging of air or of methyl chloride and without the addition of air.

When the reactor is restored to atmospheric pressure at the end of reaction, immediate polymerization of the reaction mixture takes place. It is believed that this polymerization is partly caused by the evaporation of the excess methyl chloride dissolved in the reaction mixture, with which the dissolved oxygen is then entrained, thus producing an oxygen deficiency in the reaction mixture.

EXAMPLE 2 (comparative)

Preparation of a 75% strength aqueous solution of methacryloyloxyethyltrimethylammonium chloride 360 kg of dimethylaminoethyl methacrylate containing 1,000 ppm of hydroquinone methyl ether are charged into a reactor, with stirring. A pressure of 3 bars absolute is maintained in the reactor during the entire reaction period by continuously introducing 100 standard liters per hour (Nl/h) of air. The reactor pressure is controlled by outlet purges which contain unconverted methyl chloride and air.

In a first stage, methyl chloride is introduced into the reactor continuously at a rate of 10 kg/h. After 1.5 hours water and methyl chloride are introduced continuously in a water/methyl chloride weight ratio of 1.2 (ie a molar ratio of 3.3).

The reaction temperature is maintained at 40° C.

At the end of the reaction, the reactor is cooled to 20° C. and then, simultaneously with the introduction of 10 Nm³/h of air into the liquid phase, it is restored to atmospheric pressure. The excess methyl chloride, a large quantity of which is dissolved in the reaction mixture, is then immediately vaporized. Next, air is injected into the reactor for 2 hours at a rate of 10 Nm³/h in order to strip off the traces of methyl chloride and to reoxygenate the product.

The aqueous solution of quaternary salt which is thus obtained is stored at ambient temperature, with protection from light, and polymerizes after 15 days' storage.

EXAMPLE 3

Preparation of a 75% strength aqueous solution of methacryloyloxyethyltrimethylammonium chloride 360 kg of dimethylaminoethyl methacrylate stabilized with 1,500 ppm of 3,5-ditert-butyl-4-hydroxytoluene are charged with stirring into a jacketed reactor.

During the entire reaction period, that is 10 hours in all, the temperature is maintained at 50° C., and so is atmospheric pressure and a continuous air flow of 120 Nl/h at the reactor inlet and a purge flow at the reactor outlet of less than or equal to 1.2 Nm³/h, that is to say a volume ratio of the purges to the oxygen introduced into the reactor of less than or equal to 50.

Methyl chloride is introduced at a rate of 13 kg/h for one hour, ie 11.2% of the total quantity of $CH_3Cl$ required for the reaction. Water and methyl chloride are then introduced simultaneously at rates of 20 kg/h and 16 kg/h, respecitvely, ie at a water/$CH_3Cl$ molar ratio of 3.5.

As the end of the reaction approaches, that is to say after approximately 7 hours, the methyl chloride rate is gradually reduced to 3 kg/h.

Air is then injected for 2 hours at a rate of 10 Nm³/h into the manufactured product.

The 75% strength methacryloyloxyethyltrimethylammonium chloride manufactured in this way contains 0.13% of methacrylic acid and 0.75% of dimethylaminoethyl methacrylate.

When stored at ambient temperature and protected from light, this product has a stability of more than 1 year.

EXAMPLE 4 (comparative)

Preparation of a 75% strength aqueous solution of methacryloyloxyethyltrimethylammonium chloride Into a reactor charged with 360 kg of dimethylaminoethyl methacrylate stabilized with 1,500 ppm of 3,5-ditert-butyl-4-hydroxytoluene, 30 Nl/h of air are introduced continuously during the entire operation and a temperature of 50° C., atmospheric pressure and an outlet purge rate not exceeding 1 Nm³/h are maintained for its entire duration. The volume ratio of the purges to the oxygen at the inlet of the reactor is then 166.

13 kg of methyl chloride, ie. 11.2% of the total quantity of $CH_3Cl$ required for the reaction, are introduced over 1 hour. Water and methyl chloride are then injected simultaneously at rates of 20 kg/h and 16 kg/h, respectively, ie in a water/CH3Cl molar ratio of 3.5.

As the end of the reaction approaches, the methyl chloride rate is reduced to 10 kg/h and the outlet purge rate rases up to 4.5 Nm³/h for a period of the order of 15 minutes to 1 hour. After the introduction of methyl chloride has been stopped, air is injected into the manufactured product at a rate of 10 Nm³/h for 2 hours.

The final product, stored under protection from light and at ambient temperature, has a polymerization stability which varies with time from 4 weeks to several months.

EXAMPLES 5 to 7

Preparation of a 75% strength aqueous solution of methacryloyloxyethyltrimethylammonium chloride Influence of the concentration of quaternary salt present in the first stage (a) of the process according to the invention.

Apart from the indications given in the table below, the operating conditions are identical to those used in Example 3.

The notation used in the attached table is as follows:
(I): methacryloyloxyethyltrimethylammonium chloride
(II): dimethylaminoethyl methacrylate
(III): methyl chloride
(IV): methacrylic acid

*In tests 6 and 7 an uncontrollable rise of 5° to 10° C., or even greater, is observed in the temperature of the reaction medium in the reactor after water has been introduced for 1 hour (stage b). This phenomenon is connected with the supersaturation of the reaction mixture in quaternary salt (I), thus limiting the heat exchanges with the heat transfer fluid circulating in the reactor jacket. As a result, the operating conditions in tests 6 and 7 (see the attached table) cannot be maintained until the end of the reaction. Dilution of the reaction medium with water and stoppage of $CH_3Cl$ injection are necessary during the reaction (stage b) in order to come closer to the operating conditions of test No. 5. In fact, in test No. 5, the stable operating conditions in the reactor during the reaction are an advantage. In addition, the product obtained has excellent storage stability.

EXAMPLE 8

Preparation of an 80% strength aqueous solution of methacryloyloxyethyltrimethylammonium chloride 5,220 kg of dimethylaminoethyl methacrylate stabilized with 1,500 ppm of 3,5-ditert-butyl-4-hydroxytoluene and 160 ppm of hydroquinone methyl ether are charged into an industrial reactor of 8 m³ capacity, fitted with a jacket and a stirring device, which is operating. 2,000 Nl/h of air are injected continuously into the reactor during the entire reaction period. In addition, a temperature of 50° C., atmospheric pressure, and an outlet purge (methyl chloride+air) rate of between 2,000 and 7,000 Nl/h are maintained during the reaction. The volume ratio of the purges to the oxygen introduced into the reactor thus varies between 5 and 17.5.

During the first stage of the reaction, 170 kg of methyl chloride are injected continuously into the reactor at a rate of 100–110 kg/h, ie. 10% of the total quantity of methyl chloride required for the reaction.

Methyl chloride and water are then simultaneously introduced continuously in a water/$CH_3Cl$ weight ratio of 1.2 (ie a water/$CH_3Cl$ molar ratio of 3.3).

As the end of the reaction approaches, after 12 hours the methyl chloride rate is gradually reduced to 35 kg/h while the outlet purge rate is kept below 12,000 Nl/h.

The volume ratio of the purges to the oxygen introduced into the reactor is therefore 30.

The operation is stopped after approximately 14 h of reaction.

1,720 kg of water and 1,770 kg of methyl chloride were used for this operation and 8,500 kg of methacryloyloxyethyltrimethylammonium chloride at a concentration of 80% in water were obtained.

The product obtained is then subjected to air injection at a rate of 70 Nm³/h for 1.5 h at 45°–50° C. and then for 2 hours at ambient temperature, in order to remove the dissolved methyl chloride.

The final product obtained has the following characteristics: (quantities given in %)

| water: | 20 |
|---|---|
| methacrylic acid: | 0.13 |
| dimethylaminoethyl methacrylate: | 0.14 |
| methyl chloride: | 40 ppm |
| polymer: | none |

The product manufactured in this way has a storage stability of more than 1 year.

EXAMPLE 9

Preparation of an 80% strength aqueous solution of acryloyloxyethyltrimethylammonium chloride 5,150 kg of dimethylaminoethyl acrylate stabilized with 700 ppm of hydroquinone methyl ether are charged into a stirred and jacketed industrial reactor of 8 m³ capacity.

During the entire reaction period 2,000 Nl/h of air are continuously injected into the reactor and the following are maintained:

a temperature of 50° C.,
atmospheric pressure, and
an outlet purge rate of less than 7,000 Nl/h (ie a volume ratio of purges to oxygen introduced into the reactor of less than 17.5).

In the first stage, 180 kg of methyl chloride are injected into the reactor at a rate of 110 kg/h (ie 11% of the total quantity of CH³Cl required for the reaction) and then, in a second stage, methyl chloride and water are simultaneously and continuously injected in a water/CH₃Cl weight ratio of between 0.9 and 1.0 (giving a water/CH₃Cl molar ratio of between 2.5 and 2.8).

As the end of the reaction approaches, the methyl chloride rate is gradually reduced to 35 kg/h and the outlet purge rate is maintained below 12,000 Nl/h (giving a volume ratio of the purges to the oxygen at the reactor inlet of less than 30).

The operation is stopped after 15 hours' reaction.

1,749 kg of water and 1,961 kg of methyl chloride were used in this operation and 8,260 kg of acryloyloxyethyltrimethylammonium chloride are recovered at a concentration of 80% in water.

The final product is then subjected to an injection of air at a rate of 70 Nm³/l for 1.5 h while hot and then for 1.5 h at ambient temperature.

The final product obtained has the following characteristics: (quantities given in %)

| water: | 20.4 |
|---|---|
| acrylic acid: | 0.69 |
| dimethylaminoethyl acrylate: | 1.3 |
| methyl chloride: | 15 ppm |
| polymer: | none |

This product, stored at ambient temperature and protected from light, has a stability of more than 1 year.

EXAMPLE 10

Preparation of an 80% aqueous solution of methacryloyloxyethylbenzylmethylammonium chloride 250 kg of dimethylaminoethyl methacrylate stabilized with 1,500 ppm of BHT are charged with stirring into a jacketed reactor.

During the entire reaction period, ie 6 hours in all, a temperature of 50° C. and a continuous air flow of 120 Nl/h are maintained.

Benzyl chloride is introduced at a rate of 30 kg/h for 1 hour, ie 14.9% of the total quantity required. Water and benzyl chloride are then introduced simultaneously at rates of 23 kg/h and 46 kg/h, respectively, ie in a water/benzyl chloride molar ratio of 3.5.

201 kg of benzyl chloride and 113 kg of water are introduced in all.

The 80% ammonium salt thus manufactured contains 0.3% of methacrylic acid and 0.3% of dimethylaminoethyl methacrylate.

This product is stable for over a year when stored.

EXAMPLE 11

Preparation of an 80% strength aqueous solution of acryloyloxyethyltrimethylammonium chloride 4,500 kg of dimethylaminoethyl acrylate stabilized with 700 ppm of hydroquinone methyl ether, and 1,100 kg of an 80% strength aqueous solution of acryloyloxyethyltrimethylammonium chloride are initially charged into a jacketed 8-m³ industrial reactor.

Methyl chloride and water are then introduced simultaneously and continuously into the reactor at weight flow ratios of between 1.0/1.0 and 0.9/1.0.

The reaction is conducted at atmospheric pressure, at a temperature of 52° C. and with continuous introduction of 2,000 Nl/h of air into the reactor. The residual gas rate is maintained below 7,000 Nl/h.

As the end of the reaction approaches, the methyl chloride rate is gradually reduced to 20 kg/h and the outlet purge rate is kept below 12,000 Nl/h.

The reaction is finished after 13 hours' addition of methyl chloride.

After injection of air for 3 hours at a rate of 60 Nm³/h, the finished product has the following characteristics:

| water: | 20.10% |
|---|---|
| acrylic acid: | 0.85% |
| dimethylaminoethyl acrylate: | 1.20% |
| methyl chloride: | 10 ppm |
| polymer: | none |

The product offers a storage stability of over 1 year.
The total quantities used in this operation were:
4,500 kg of Adame
1,100 kg of Adquat MC 80
1,685 kg of methyl chloride
1,522 kg of water
and 8,625 kg of Adquat MC 80 are recovered.

APPENDIX: TABLE

| Test No. | Stage a (duration: 1 h) | | Stage b | | Impurities present in the final product | |
|---|---|---|---|---|---|---|
| | Quantities of reactants introduced (kg) | Composition of the mixture obtained (%) | (III) introduced (kg/h) | Water introduced (kg/h) | Content of (II) (%) | Content of (IV) (%) |
| 5 | (II): 360 (III): 10 | (I): 10 (II): 90 | 20 | 20 | 0.15 | 0.13 |
| 6* | (II): 360 (III): 30 | (I): 30 (II): 70 | 20 | 30 | 0.15 | 0.12 |
| 7* | (II): 360 (III): 40 | (I): 40 (II): 60 | 20 | 40 | 0.15 | 0.12 |

We claim:

1. A process for the preparation of an aqueous solution of unsaturated quaternary ammonium salts corresponding to the following formula (I):

$$H_2C=C(R_3)-C(O)-A-R_4-N(R_1)(R_2)(R).X$$

in which:
A is an oxygen atom or an NH group,
$R_3$ is a hydrogen atom or a methyl radical,
$R_4$ is a linear or branched alkyl radical containing from 2 to 4 carbon atoms,
$R_1$ and $R_2$, which are different or identical, are an alkyl radical or an aryl radical,
R is an alkyl or aryl radical, and
X is chosen from Cl, Br, I, $CH_3-CO_3$ or $CH_3-SO_4$, from at least one (meth)acrylic monomer (II) of the formula:

$$H_2C=C(R_3)-C(O)-A-R_4-N(R_1)(R_2)$$

and at least one quaternizing agent III of the formula RX, in the presence of at least one polymerization inhibitor, the process comprising:
(a) reacting the (meth)acrylic monomer (II) in a closed reactor with 5 to 20% of the weight quantity of quaternizing agent (III) required for the reaction, wherein the latter agent is introduced into the reactor continuously,
(b) next, adding water and the remainder of the quaternizing agent (III) continuously until the required concentration of quaternary ammonium salt (I) in water is obtained,
(c) during the stages (a) and (b), maintaining the temperature at a value of between 30° and 60° C., and
(d) during the stages (a) and (b) and as the end of the reaction approaches, maintaining a stream of gas containing oxygen in the reaction mixture, such that the volume ratio of gas at the reactor outlet to the oxygen introduced at the inlet of this same reactor is less than 100/1.

2. The process as claimed in claim 1, wherein the temperature is between 45° C. and 55° C. during stages (a) and (b).

3. The process as claimed in claim 1 wherein 10% by weight of quaternizing agent are introduced during stage (a).

4. The process as claimed in claim 1, wherein the reaction is carried out at an absolute pressure between atmospheric pressure and 1.6 bars.

5. The process as claimed in claim 1 wherein the reactor outlet gas is conveyed to a processing device intended to free it from traces of quaternizing agent RX, which consists of a second quaternization reactor containing the (meth)acrylic monomer.

6. The process as claimed in claim 1 wherein from 100 to 1,500 ppm of polymerization inhibitor are used based on the meth(acrylic) monomer.

7. A process for the preparation of an aqueous solution of unsaturated quaternary ammonium salts corresponding to the following formula (I):

$$H_2C=C(R_3)-C(O)-A-R_4-N(R_1)(R_2)(R).X$$

in which:
A is an oxygen atom or an NH group,
$R_3$ is a hydrogen atom or a methyl radical,
$R_4$ is a linear or branched alkyl radical containing from 2 to 4 carbon atoms,
$R_1$ and $R_2$, which are different or identical, are an alkyl radical or an aryl radical,
R is an alkyl or aryl radical, and
X is chosen from Cl, Br, I, $CH_3-CO_3$ or $CH_3-SO_4$, from at least one (meth)acrylic monomer (II) of the formula:

$$H_2C=C(R_3)-C(O)-A-R_4-N(R_1)(R_2)$$

and at least one quaternizing agent (III) of the formula RX, in the presence of at least one polymerization inhibitor, the process comprising:
(a) introducing the (meth)acrylic monomer (II) and 5 to 20% by weight, based on said monomer, of an aqueous solution of quaternary salt (I) containing 50 to 80% by weight of quaternary salt into a closed reactor,
(b) continuously adding water and the remainder of the quaternizing agent (III) until the required concentration of quaternary ammonium salt (I) in water is obtained,
(c) during the stages (a) and (b), maintaining the temperature at a value of between 30° and 60° C., and
(d) during the stages (a) and (b) and especially as the end of the reaction approaches, maintaining a stream of gas containing oxygen in the reaction mixture, such that the volume ratio of gas at the reactor outlet to the oxygen introduced at the inlet of this same reactor is less than 100/1.

8. The process as claimed in claim 7, wherein the temperature is maintained between 45° C. and 55° C. during stages (a) and (b).

9. The process as claimed in claim 7 wherein 10% by weight of an aqueous solution of quaternary salt containing 50 to 80% by weight of quaternary salt are introduced during stage (a).

10. The process as claimed in claim 7, 8 wherein the reaction is carried out at an absolute pressure between atmospheric pressure and 1.6 bars.

11. The process as claimed in claim 7 wherein the reactor outlet gas is conveyed to a processing device intended to free it from traces of quaternizing agent RX which consists of a second quaternization reactor containing the (meth)acrylic monomer.

12. The process as claimed claim 7, wherein from 100 to 1,500 ppm of polymerization inhibitor are used based on the (meth)acrylic monomer.

13. The process as claimed in claim 2, wherein 10% by weight of quaternizing agent are introduced during stage (a).

14. The process as claimed in claim 2, wherein the reaction is carried out at an absolute pressure between atmospheric pressure and 1.6 bars.

15. The process as claimed in claim 3, wherein the reaction is carried out at an absolute pressure between atmospheric pressure and 1.6 bars.

16. The process as claimed in claim 13, wherein the reaction is carried out at an absolute pressure between atmospheric pressure and 1.6 bars.

17. The process as claimed in claim 2, wherein the reactor outlet gas is conveyed to a processing device intended to free it from traces of quaternizing agent RX, which consists of a second quaternizing agent reactor containing the (meth)acrylic monomer.

18. The process as claimed in claim 2, wherein from 100 to 1,500 ppm of polymerization inhibitor are used based on the meth(acrylic) monomer.

19. The process as claimed in claim 3, wherein from 100 to 1,500 ppm of polymerization inhibitor are used based on the meth(acrylic) monomer.

20. The process as claimed in claim 4, wherein from 100 to 1,500 ppm of polymerization inhibitor are used based on the meth(acrylic) monomer.

21. The process as claimed in claim 8, wherein 10% by weight of an aqueous solution of quaternary salt containing 50 to 80% by weight of quaternary salt are introduced during stage (a).

22. The process as claimed in claim 8, wherein the reaction is carried out at an absolute pressure between atmospheric pressure and 1.6 bars.

23. The process as claimed in claim 8, wherein the reactor outlet gas is conveyed to a processing device intended to free it from traces of quaternizing agent RX which consists of a second quaternization reactor containing the (meth)acrylic monomer.

24. The process as claimed in claim 9, wherein the reactor outlet gas is conveyed to a processing device intended to free it from traces of quaternizing agent RX which consists of a second quaternization reactor containing the (meth)acrylic monomer.

25. The process as claimed in claim 10, wherein the reactor outlet gas is conveyed to a processing device intended to free it from traces of quaternizing agent RX which consists of a second quaternization reactor containing the (meth)acrylic monomer.

26. The process as claimed in claim 8, wherein from 100 to 1,500 ppm of polymerization inhibitor are used based on the (meth)acrylic monomer.

27. The process as claimed in claim 9, wherein from 100 to 1,500 ppm of polymerization inhibitor are used based on the (meth)acrylic monomer.

28. The process as claimed in claim 10, wherein from 100 to 1,500 ppm of polymerization inhibitor are used based on the (meth)acrylic monomer.

29. The process as claimed in claim 11, wherein from 100 to 1,500 ppm of polymerization inhibitor are used based on the (meth)acrylic monomer.

30. The process as claimed in claim 12, wherein from 100 to 1,500 ppm of polymerization inhibitor are used based on the (meth)acrylic monomer.

31. In a process for the preparation of an aqueous solution of unsaturated quaternary ammonium salts coresponding to the following formula (I):

$$H_2C=C(R_3)-C(O)-A-R_4-N(R_1)(R_2)(R).X$$

in which:
A is an oxygen atom or an NH group,
$R_3$ is a hydrogen atom or a methyl radical,
$R_4$ is a linear or branched alkyl radical containing from 2 to 4 carbon atoms,
$R_1$ and $R_2$, which are different or identical, are an alkyl radical or an aryl radical,
R is an alkyl or aryl radical, and
X is chosen from Cl, Br, I, $CH_3-CO_3$ or $CH_3-SO_4$, from at least one (meth)acrylic monomer (II) of formula:

$$H_2C=C(R_3)-C(O)-A-R_4-N(R_1)(R_2)$$

and at least one quaternizing agent (III) of formula RX, in the presence of at least one polymerization inhibitor, the improvement wherein:
the reaction between the (meth)acrylic monomer (II) and the quaternizing agent (III) is conducted in a reactor containing in inlet and outlet, and at least during near the end of the reaction, in the presence of a stream of gas containing oxygen, such that the volume ratio of gas at the reactor outlet to the oxygen introduced at the inlet of the same reactor is less than 100/1.

32. A process of claim 31 wherein said volume ratio is less than 50/1.

33. A process of claim 1 wherein, in step (b), said water and said quaternizing agent (III) are added at a molar ratio of between 2.2-3.7.

34. A process of claim 7 wherein, in step (b), said water and said quaternizing agent (III) are added at a molar ratio of between 2.2-3.7.

35. A process of claim 1 wherein steps (a) and (b) are conducted at a temperature of between 45°-55° C.

36. A process of claim 7 wherein steps (a) and (b) are conducted at a temperature of between 45°-55° C.

37. A process of claim 31 wherein said process is conducted at a pressure of from atmospheric pressure to 1.6 bars absolute pressure.

38. A process of claim 31 wherein, at the end of the reaction, remaining quaternizing agent (III) dissolved in the reaction mixture is removed by purging the latter with a stream of oxygen-containing gas.

39. A process of claim 31 wherein the concentration of quaternary salt (I) in water at the end of the reaction is from 50-85%.

40. A process of claim 31 wherein said reactor has a capacity of from 20-50 m³.

* * * * *